US008178315B2

(12) United States Patent
Bush et al.

(10) Patent No.: US 8,178,315 B2
(45) Date of Patent: May 15, 2012

(54) LYOPHILIZED EDIBLE FOOD INCORPORATING A MARKER AND METHODS OF MAKING

(75) Inventors: Kerry C. Bush, Brentwood, TN (US); Keith D. Evans, Brentwood, TN (US); Stanley J. Konopka, Franklin, TN (US)

(73) Assignee: Advanced Breath Diagnostics, LLC, Brentwood, TN (US)

(*) Notice: Subject to any disclaimer, the term of this patent is extended or adjusted under 35 U.S.C. 154(b) by 330 days.

(21) Appl. No.: 12/121,116

(22) Filed: May 15, 2008

(65) Prior Publication Data

US 2008/0286200 A1 Nov. 20, 2008

Related U.S. Application Data

(63) Continuation-in-part of application No. 10/435,092, filed on May 9, 2003, now Pat. No. 7,758,569.

(60) Provisional application No. 60/379,581, filed on May 10, 2002.

(51) Int. Cl.
*A61K 49/00* (2006.01)
*A61K 35/54* (2006.01)

(52) U.S. Cl. ........ 435/29; 424/9.2; 424/1.61; 424/581; 424/195.17

(58) Field of Classification Search .................. None
See application file for complete search history.

(56) References Cited

U.S. PATENT DOCUMENTS

| | | | |
|---|---|---|---|
| 4,985,232 A | 1/1991 | Jacobssen | |
| 5,707,602 A * | 1/1998 | Klein | 424/1.17 |
| 5,785,949 A | 7/1998 | Klein | |
| 6,432,382 B1 | 8/2002 | Mehta | |
| 6,548,043 B1 | 4/2003 | Wagner | |
| 6,740,305 B1 | 5/2004 | Ajami | |
| 2007/0014718 A1 | 1/2007 | Kagami | |

FOREIGN PATENT DOCUMENTS

| | | | |
|---|---|---|---|
| GB | 2360845 | | 10/2001 |
| GB | 2360845 A | * | 10/2001 |
| WO | 97/35622 | | 10/1997 |
| WO | 01/72342 | | 10/2001 |

OTHER PUBLICATIONS

Lee et al, "A valid, accurate, office-based non-radioactive test for gastric emptying of solids," (Gut), Jun. 2000, vol. 46, Issue 6, pp. 768-773.*
B.E. Viramontes, et al., "Validation of a Stable Isotope Gastric Emptying Test for Normal, Accelerated or Delayed Gastric Emptying" Neurogastroenterol. Mot. (2001) 13, 567-574.
Yvo F. Ghoos, et al., "Measurement of Gastric Emptying Rate of Solids by Means of a Carbon-Labeled Octanoic Acid Breath Test" Gastroenterology 1993;104:1640-1647.
J S Lee, et al., "A Valid, Accurate, Office Based Non-Radioactive Test for Gastric Emptying of Solids," Gut 2000; 46:768-773.
Abell et al., "Treatment of gastroparesis: a multidisciplinary clinical review", Neurogastroenterol Motil (2006) 18, 263-283.
B. Rosner, On the Detection of Many Outliers, Technometrics, 17/2, 221-227 (1975).
Breidthardt et al., "Medical and Economic Long-term Effects of B-type Natriuretic Peptide Testing in Patients with Acute Dyspnea", Clinical Chemistry 53:8 (2007), 1415-1422.
Bytzer et al., "GI Symptoms in Diabetes Mellitus are Associated with Both Poor Glycemic Control and Diabetic Complications" Am J Gastroenterology; 2002, vol. 97, No. 3, pp. 604-611.
Bytzer et al., "Prevalence of gastrointestinal symptoms associated with diabetes mellitus: a population-based survey of 15,000 adults," Arch Intern Med 2001; 161:1989-1996.
Chamorro et al., "Pharmacology and toxicology of *Spirulina alga*," Rev Invest Clin Sep.-Oct. 1996; 48(5):389-99.
Chamorro et al., "Subchronic toxicity study in rats fed *spirulina*," J. Pharm Belg., 1988, 43, 1, 29-36.
Ciferri et al., "*Spirulina* the Edible Microorganism," Microbiological Reviews, Dec. 1983, p. 551-578.
Coste et al., "A Gray Zone Assigned to Inconclusive Results of Quantitative Diagnostic Tests: Application to the Use of Brain Natriuretic Peptide for Diagnosis of Heart Failure in Acute Dyspneic Patients", Clinical Chemistry 52:12 (2006), 2229-2235.
Enck et al., "Prevalence of gastrointestinal symptoms in diabetic patients and non-diabetic subjects," Z Gastroenterol 1994; 32:637-641.
FDA Talk Paper, "*Spirulina*", Jun. 23, 1981.
Feinstein, "The inadequacy of binary models for the clinical reality of three-zone diagnostic decisions", J Clin Epidemiol, 43, 109-113 (1990).
Harris, et al., Statistical Bases of Reference Values in Laboratory Medicine, Marcel Dekker, 1995, Chapter 8: Analytical Goals for Reference Values.
Janatuinen et al., "Gastrointestinal symptoms in middle-aged diabetic patients," Scan J Gastroenterol 1993; 28:427-432.
Krishnakumari et al., "Food safety evaluation: acute oral and dermal effects of the algae *Scenedesmus acutus* and *Spirulina platensis* on albino rats", J. of Food Protection, vol. 44, No. 12, Dec. 1981, 934-935.
Lidums et al., "Effect of atropine on proximal gastric motor and sensory function in normal subjects", Gut 2000; 47:30-6.
Maleki et al., "Gastrointestinal tracts symptoms among persons with diabetes mellitus in the community," Arch Intern Med 2000; 160:2808-2816.
Park et al., "Clinical Reviews: Gastroparesis: Clinical Update" American Journal of Gastroenterology, ISSN 0002-9270 (2006), 1129-1139. R.S. Chhikara et al, Extended critical Values of Extreme Studentized Deviate Test Statistics for Detecting Multiple Outliers, Commun. Statist.-Simula. Computa., B9(2), 155-166 (1980).
Salazar et al., "Effect of *Spirulina maxima* consumption on reproduction and peri- and postnatal development in rats," Food and Chemical Toxicology, 34 (1996) 353-359.

(Continued)

*Primary Examiner* — Lisa J Hobbs
(74) *Attorney, Agent, or Firm* — Fredrikson & Byron, P.A.

(57) ABSTRACT

A standardized, lyophilized edible food containing a biologically safe stable marker for use in the measurement of gastric emptying by the quantification of marker excreted in the breath of the patient.

43 Claims, No Drawings

OTHER PUBLICATIONS

Schofield, "Predicting basal metabolic rate, new standards and review of previous work", Hum Nutr Clin Nutr (1985) 39, 541.

Solberg, "RefVal: a program implementing the recommendations of the International Federation of Clinical Chemistry on the statistical treatment of reference values", Computer Methods and Programs in Biomedicine 1995, 48:247-256.

Szarda et al. "A Stable Isotope Breath Test with a Standard Meal for Abnormal Gastric Emptying of Solids in the Clinic and in Research", Clinical Gastroenterology and Hepatology, 2008; 6:635-643.

Talley et al., "Effects of a motilin receptor agonist (ABT-229) on upper gastrointestinal symptoms in type 1 diabetes mellitus: a randomized, double-blind, placebo controlled trial," Gut 2001; 49:395-401.

Talley et al., "Epidemiology of colonic symptoms and the irritable bowel syndrome," Gastroenterology 101:927-934, 1991.

Taub et al, "Irritable bowel syndrome defined by factor analysis. Gender and race comparisons." Dig Dis Sci 40:2647-2655, 1995.

Yoshino et al., "The chronic intoxication test of *Spirulina* product fed to wistar rats," Japanese Journal of Nutrition, 38 (5), 1980, 221-226.

Zuckerman et al., "Healthcare-seeking behaviors related to bowel complaints. Hispanics versus non-Hispanic whites." Dig Dis Sci 41:77-82, 1996.

Bytzer et al., "Gastrointestinal symptoms in Diabetes Mellitus are Associated with Diabetic Complications but not with Current Glycemic Control," Abstract from Digestive Disease Week (DDW) 2000; Gastroenterology 2000; 118:A468.

\* cited by examiner

LYOPHILIZED EDIBLE FOOD INCORPORATING A MARKER AND METHODS OF MAKING

CROSS REFERENCE TO RELATED APPLICATIONS

This application claims priority to U.S. utility patent application Ser. No. 10/435,092, filed May 9, 2003, which in turn claims priority to U.S. provisional patent application No. 60/379,581, filed May 10, 2002, the entire contents of each of which are incorporated herein by reference.

FIELD OF THE INVENTION

This invention relates generally to a lyophilized (freeze-dried) meal including an edible food, a component of which includes a marker or drug and methods for using same for reliably delivering a marker or drug into a mammal and the use of that meal for measuring the absorption of therapeutic and diagnostic drugs or markers across an array of highly standardized meals. It also relates to a method of validating a meal to be used in diagnostic or test methods. Furthermore, the meal may be used to measure bodily (physiological) functions as a result of the digestion, absorption and/or metabolism of the meal and its marker or drug.

BACKGROUND OF THE INVENTION

Digestion of consumed foodstuffs begins in the oral cavity where food is mechanically broken down by mastication, lubricated with saliva, and enzymatically processed by amylase present in the saliva. Digestion continues in the stomach where food is liquefied by gastric juices and enzymes secreted by the cells lining the stomach to produce chyme. Chyme enters the small intestine via the pyloric sphincter for further processing by bile salts produced by the liver and pancreatic digestive enzymes. Components not absorbed by or transported into the small intestine are subject to subsequent processing in the large intestine.

The rate at which chyme travels to the small intestine (gastric emptying rate) is the product of numerous physiological factors including, hormones, chemical signals in the ingesta, as well as signals from the nervous system.

A number of the population are affected by disorders that affect the emptying rate. For example, when the rate is accelerated, undigested food is prematurely dumped from the stomach to the small intestine. Conversely, when the rate is decelerated, the movement of ingested food from the stomach to the small intestine is delayed, giving rise to the condition termed "delayed emptying" otherwise known as gastroparesis.

Disorders involving gastric emptying rate are typically diagnosed by monitoring the rate at which a meal empties the stomach and enters the small intestine. In these tests, typically, an edible food is used to transport a marker into the gut of an animal and gastric emptying monitored by the marker.

Currently, the routine (gold standard) method for quantifying gastric emptying in humans is quantitative gastric scintigraphy. Scintigraphy involves the ingestion of a meal including at least one edible food, a component of which has been radiolabeled, and the subsequent measurement of gamma emission by a scintillation camera (positioned over the stomach) as the labeled food is emptied from the stomach.

The most common type of meal used in scintigraphy measurement of gastric emptying is a meal typically made by cooking 0.5 mCi $^{99m}$Tc sulphur colloid with two raw eggs or 120 grams of a liquid egg substitute such as the product sold by ConAgra under the trademark Egg Beater®. In typical use, the patient fasts the night before the test. At the time of the test the patient consumes the cooked radiolabeled egg component with two slices of bread, 30 grams of jam and 120 ml of water. Scintigraphic scanning with anterior and posterior cameras is performed immediately after the test meal is consumed and scans are obtained every 15 minutes for two hours and every 30 minutes for up to six hours. Scintigraphy measurements of gastric emptying are direct, since the camera directly measures the meal exiting the stomach.

Scintigraphic results may be reported as "Percent Meal Emptied" or inversely, "Percent Meal Retained." Typically, the % meal retained is calculated and reported at the 1, 2, 3, and 4 hour time point based on the amount of gamma radiation appearing at each respective time point. With time, more and more of the meal is emptied and hence there is less and less gamma radiation to be observed from the stomach. An evolving scintigraphic metric in the GI community defines slow gastric emptying as >10% of a meal remaining at the 4-hour time point when utilizing ~225 kcal meal that has been demonstrated to empty in about 4 hours in healthy individuals. The greater the percent retained, the slower the gastric emptying rate. Two additional parameters are clinically useful in scintigraphic scanning. The first, $t_{LAG}$, is the time required for the first 10% of the food to empty from the stomach. The second, $t_{1/2}$, is the time required for half of the contents to be emptied from the stomach. Percent gastric retention of the radiolabel is calculated at each time point to generate a scintigraphic gastric retention curve. The curve is mathematically modeled with a power exponential model and the diagnostic result $t_{LAG}$ and $t_{1/2}$ can be calculated from the curve.

Several disadvantages are associated with the traditional scintigraphy method. First, patients must be subjected to radioisotopes. This is particularly problematic for women of childbearing age or children. Further, the procedure must be carried out at specialized nuclear medicine facilities. Finally, the preparation for the procedure is cumbersome and potentially can introduce error to the test procedure. Prior to the procedure, personnel must prepare the labeled meal. Because cooking parameters or food quality, consistency and meal matrix may vary from hospital to hospital, standardization is lacking. For example, the caloric value, the matrix of meal and amount of scintigraphic scanning time vary from testing center to testing center. As with any medical test, standardization is of significant importance in gastric emptying test procedures.

Recently, a method for measuring gastric emptying has been described that utilizes an edible food labeled with non-radioactive markers. As the non-radioactive labeled edible food is digested, a labeled component is produced which can be detected in the patient's breath. This method is described in detail in U.S. Pat. No. 5,707,602, the teachings of which are hereby incorporated by reference. This patent describes the use of a nutritional supplement, *Spirulina platensis*, a blue green algae, grown in a highly enriched $^{13}CO_2$ environment. The $^{13}$Carbon incorporated into the algal biomass acts as a non-radioactive marker. A small amount of the labeled algae is baked into a roll or breakfast bar and consumed by a patient with juice or water. The meal is triturated by the stomach to a particle size of approximately 1-2 mm and then passes from the stomach through the pylorous into the intestine. In the intestine, the labeled products of $^{13}$C-*Spirulina platensis* digestion are absorbed and metabolized giving rise to labeled carbon dioxide expired in the breath. The rate of $^{13}CO_2$ appearance in the patient's breath ($^{13}CO_2$ excretion rate) is correlated to the rate of gastric emptying.

In contrast to scintigraphy, measurement of gastric emptying, in accordance with the marker described above, is indirect. Therefore, it is desirable to mathematically correlate the $^{13}CO_2$ excretion curve to the scintigraphic gastric retention curve so that the emptying time of the stomach can be calculated from the $^{13}CO_2$ curve. For example, one can use a general linear model to develop the relationship between diagnostic parameters obtained from scintigraphic measurements and the corresponding data obtained from the patient's $^{13}CO_2$ excretion rate when both the radioactive scintigraphic label and $^{13}C$-label are administered simultaneously in the same meal.

To accurately correlate the $^{13}CO_2$ excretion curve and the scintigraphic decay curve (which allows one to generate a predictive mathematical model from which the gastric emptying rate may be calculated using only $^{13}CO_2$ excretion data), it is desirable to standardize the edible food and/or meal matrix delivering the marker to reduce the number of interfering variables. For example, if the new marker or drug (the surrogate marker) is incorporated into an edible food and/or meal (surrogate meal) that is different than the edible food and/or meal in which the well accepted marker or drug (predicate) is incorporated (predicate meal) the correlation process may be more difficult and/or have poor predictive value. Thus, it is desirable for the predicate and surrogate meals to be as similar in composition, texture and nutritional content to each other as possible.

Similarly, such standardization allows for the validation of novel diagnostic or medical tests against well known, accepted tests ensuring accuracy and acceptance within the medical community. This may be particularly important where the new test detects, assesses, or measures physiological characteristics in a different manner, for example, indirectly versus directly.

In addition to standardization between novel and traditional medical tests, it is desirable that each individual method be standardized. It is desirable and often essential, that a medical test be performed identically each time it is conducted.

Thus, it is an object of the present invention to ensure reliability, reproducibility, accuracy and standardization when delivering a meal combined with a diagnostic marker or therapeutic drug into or beyond the stomach. It is further an object to provide a reliable method of validating the performance of the novel (surrogate) marker and measuring the absorption and/or activity of the drug or marker.

SUMMARY OF THE INVENTION

Some embodiments provide a method of producing a standardized edible food labeled with a marker comprising the sequential steps of: providing a marker, uniformly distributing a known amount of said marker throughout an edible food component, and lyophilizing the marker and the edible food component. The marker can be produced through a biomass such as *Spirulina platensis*. The edible food component can comprise whole eggs, for example whole eggs that are part of a liquid egg formulation. The method can also include reconstituting the marker and edible food component and adding a radioactive isotope such as $^{99m}Tc$ sulphur colloid.

Other embodiments provide a method of producing a standardized edible food labeled with markers comprising the sequential steps of: providing a first marker and a second marker, the first marker comprising biomass and the second marker comprising a radioactive isotope, uniformly distributing a known amount of the first marker throughout an edible food component, lyophilizing the first marker and the edible food component, reconstituting the first marker and the edible food component, and adding the second marker to the first marker and the edible food component. The first marker can be *Spirulina platensis* and the second marker can be $^{99m}Tc$ sulphur colloid. The edible food component can also comprise whole eggs, such as whole eggs that are part of a liquid egg formulation.

Other embodiments provide a method of producing a standardized meal labeled with a marker comprising the sequential steps of: providing an edible food component, lyophilizing the edible food component, reconstituting the edible food component, adding a marker to the reconstituted edible food component, and lyophilizing the marker and the reconstituted edible food component. The standard meal can have a % binding recovery that is substantially equal to a % binding recovery of a control meal, wherein the control meal comprises a lyophilized edible food component that has been lyophilized only once. In some cases, the % binding recovery is at least 100%. The method can also comprise dividing the edible food component into sub-batches after lyophilizing the edible food component, and wherein the reconstituting the edible food component comprises reconstituting one or more sub-batches. The marker can be a biomass, such as *Spirulina platensis*. The edible food component can also comprise whole eggs.

Other embodiments provide a meal comprising an edible food component, a known amount of a marker uniformly distributed throughout the edible food component, said marker being a $^{13}C$ marker derived from a biomass and chosen so that when ingested by a mammal with the meal either the absorption or metabolism of the marker may be monitored and correlated to a physiological function of the mammal or a therapeutically effective amount of the marker delivered to the mammal, wherein the edible food component has been lyophilized and reconstituted before said known amount of marker is uniformly distributed throughout the edible food component, and wherein the edible food component and the marker have been lyophilized together after said known amount of marker is distributed throughout the edible food component, so that the edible food component has been lyophilized twice. In some cases, the meal has a % binding recovery that is substantially equal to the % binding recovery of a control meal, wherein the control meal comprises an edible food component that has been lyophilized only once. For example, the meal can have a % binding recovery that is at least 100%. The edible food component can comprise whole eggs, such as whole eggs that are part of a liquid egg formulation. The biomass can also be $^{13}C$-enriched *Spirulina platensis*.

Other embodiments provide a meal comprising whole eggs, wherein the whole eggs are bound to a known amount of a $^{13}C$ marker derived from a biomass, said $^{13}C$ marker chosen so that when ingested by a mammal with the meal either the absorption or metabolism of the marker may be monitored and correlated to a physiological function of the mammal or a therapeutically effective amount of the marker delivered to the mammal, wherein the whole eggs have been lyophilized and reconstituted before the $^{13}C$ marker is added to the eggs, and wherein the whole eggs and $^{13}C$ marker have been lyophilized together after the marker is added to the eggs, so that the whole eggs have been lyophilized twice. The meal can have a % binding recovery that is substantially equal to the % binding recovery of a control meal, wherein the control meal comprises a whole eggs that been lyophilized only once. In some cases, the % binding recovery is at least 100%. Preferably, during trituration in a mammal's stomach substantially all of the $^{13}$C marker remains bound to the whole eggs.

DETAILED DESCRIPTION OF THE PREFERRED EMBODIMENT

A standardized gastric emptying test that is safe, efficient, diagnostically reliable, standardized, uniformly manufactured to regulatory standards suitable for oral pharmaceutical products and that can be readily used in a clinical setting may employ a stable marker such as $^{13}$C incorporated into a prepared standardized meal. A standardized freeze-dried meal uniformly labeled, easily re-constituted surrogate meal will assure more reliable performance of the test for which the meal is prepared. The terms freeze dry and lyophilize are used interchangeably herein.

The standardized meal into which the marker is to be incorporated may be any food type suitable for human consumption. For example, typical meals used for gastric emptying tests have included scrambled eggs and liver. As will be appreciated by those skilled in the art, any food item that is amen able to the freeze dry process may be utilized. Food items can be chosen to accommodate patients with special dietary needs, for example, vegetarians or those desiring food processed under Kosher standards.

In one embodiment, the standardized meal is eggs. Traditional scintigraphy methods have provided a meal consisting of a sandwich prepared with radio labeled grocery-bought eggs. Recent studies indicate that the excretion curve derived from a biologically labeled meal correlates well with the gamma emission curve. Further, eggs are amen able to the freeze drying process and have a long shelf life. Preferably, the eggs are whole eggs, which include both egg yolk and egg white.

The meal or edible food component of a meal can be labeled with a stable, biologically safe isotope, such as $^{13}$C. As will be appreciated by those skilled in the art, $^{13}$C may be provided from any source that is suitable for human consumption. For example, octanoic acid incorporating $^{13}$C may be mixed with the meal or edible food component of a meal. In one embodiment, the source of the $^{13}$C is *Spirulina platensis*. This edible blue green algae containing $^{13}$C may be obtained by growing the algal cells in a $^{13}$C-enriched environment as is disclosed in commonly assigned U.S. Pat. No. 6,872,516, the disclosure of which is herein incorporated by reference in its entirety.

The freeze-dry standardized meal can be used with a variety of markers and applied to a wide array of meal types and incorporate all types and exacting amounts of markers, including those that are directly synthesized with $^{13}$Carbon label or those derived through $^{13}$Carbon labeling of biomasses like $^{13}$C-*Spirulina platensis*.

To ensure accuracy of test results, the $^{13}$C is desirably uniformly distributed throughout the edible meal or food component thereof. In one embodiment, the meal or component thereof and $^{13}$C algae are lyophilized separately. Subsequently, a pre-measured amount of $^{13}$C algae is thoroughly mixed with a pre-measured amount of specially formulated lyophilized egg to ensure uniform distribution. Alternatively, a pre-measured amount of algae containing $^{13}$C can be thoroughly mixed with a pre-measured amount of liquid egg prior to lyophilization. In this embodiment, no onsite preparation other than reconstitution and cooking, if necessary, is required.

In some cases, the edible meal or food component is lyophilized or otherwise dried and reconstituted prior to adding a marker. For example, in some cases, a large batch of the food component is lyophilized and then divided into sub-batches. The sub-batches are then stored. Later, one or more sub-batches are reconstituted and a marker is added. Both the reconstituted food component and the marker are then mixed and lyophilized together to obtain a product that can be used in diagnostic tests.

In one embodiment, a liquid egg formulation is lyophilized or spray-dried alone to obtain a batch of blank egg powder. Suitable liquid egg formulations can be obtained from USDA certified suppliers such as Willamette Farms, located in Newberg, Oreg. Preferably, the liquid egg formulations include whole eggs. After lyophilization or drying, the batch of blank egg powder can then be divided into sub-batches and stored. Later, one or more sub-batches of blank egg powder can then be reconstituted by rehyhdrating to its original liquid form. In some cases, water is added to the blank egg powder until a liquid egg formulation containing roughly about 73% water and about 27% solids is obtained. Next, a marker is added to the rehydrated liquid egg formulation. The marker itself can be in a dry powder, suspension, crystalline or other dissolvable or dispersible form, fresh and/or frozen or lyophilized form. In some cases, the marker is a biomass such as *Spirulina platensis*. The marker can also be added in any desired amount. The marker is preferably uniformly mixed with the rehydrated liquid egg formulation. Finally, both the marker and rehydrated liquid egg formulation are lyophilized together to provide a standardized labeled lyophilized meal that can be used in gastric emptying tests.

Methods of making gastric emptying test meals wherein a single food component is lyophilized or dried multiple times have not been previously used, as such multiple lyophilizations or dryings make these methods unnecessarily complex. However, Applicant has found that such multiple lyophilizations or dryings provide economic benefits. A large amount of an edible food component, for example, specifically formulated liquid whole eggs, can be produced or obtained at one particular point in time and then lyophilized or dried into a large batch. Thus, a single large batch uniform in matrix and caloric value per the defined formulation can be obtained and processed at once, rather than repeatedly producing or obtaining food components and then lyophilizing or drying multiple small batches at different points in time. These small batches result in poor economics, and costly redundancy in quality control procedures, quality control testing, labeling, packaging and stability testing overhead. The large batch can then be divided into any desired number of sub-batches and then stored.

At a desired time, one or more sub-batches can be reconstituted and a desired amount of marker can be added and uniformly mixed throughout. The number of sub-batches that are reconstituted can be aligned closely with sales and inventory demand for diagnostic meals. In other words, when it is desired to make labeled meals, the stored sub-batches can easily be used, rather than having to produce or order fresh food components. The marker and reconstituted sub-batch(es) are then lyophilized together to provide a batch of lyophilized meal incorporating a marker. This lyophilized meal incorporating a marker can then be divided into further sub-batches or individual doses and packaged to provide a standardized meal of consistent matrix, caloric value, marker content and marker uniformity. This production process allows for a manufacturer to consistently prepare highly standardized and uniform lyophilized meals incorporating a marker more frequently and more closely aligned with sales and inventory demands.

Skilled artisans would expect that a gastric emptying meal prepared by lyophilizing or drying a food component multiple times would not work. For example, in order for meals to be successful in diagnostic tests such as solid phase gastric emptying tests, the marker should remain bound to meal components during digestion. Skilled artisans would expect that multiple lyophilizations or dryings of a food component would be detrimental to the binding and digestive characteristics of that component. For example, multiple lyophilizations or dryings would be expected to cause inconsistencies in the food component properties and cause it to lack uniformity, which would affect binding capacity of the marker to the component. However, Applicant has found that multiple lyophilization or drying steps do not negatively affect the binding capacity of the marker to the food nor the $^{13}C$-signal derived from the meal. For example, Applicant conducted a study to determine the % binding recovery of a $^{13}C$ label in a specifically formulated $^{13}C$-labeled whole egg meal that has been lyophilized twice ("the test meal") as compared to the % binding recovery in a $^{13}C$-labeled meal of the same formulation that has had its egg component lyophilized once ("the control meal"). The control meal had a binding capacity of 108.5% and the test meal had a binding capacity of 107.5%. Thus, the test meal had a % binding recovery that is substantially equal to the % binding recovery of the control meal.

The term "% binding recovery" is a term used to describe the endpoint of a functional assay used to determine how much of the $^{13}C$ signal derived from a marker remains bound to the food component(s) of the standardized meal after in-vitro digestion utilizing U.S.P gastric juice. In this assay, the meal with marker is prepared in the same manner as that delivered to the patient. Half of the meal is assayed for $^{13}C$ content prior to digestion. The isotope ratio mass spectrometry signal specific to the $^{13}C$ content in the meal is determined. The second half of the meal then undergoes simulated in-vitro human gastric digestion. Remaining solids after simulated digestion are then recovered and analyzed for $^{13}C$ content. If the label is remaining bound to the solid components of the meal matrix, the signal observed from the digested meal should be substantially equal to or greater than that of the non-digested meal.

The signal in the digested meal can be slightly higher than the pre-digested meal because the egg formulation utilized contains a small amount of skim milk solids. Although the skim milk solids contribute caloric value and taste, they are not involved in the binding of the label and are not retained in residual post-digested solids. Hence the concentration of $^{13}C$ is slightly higher in the remaining post-digested material compared to the pre-digested material originally containing the milk solids. On average, % binding across multiple batches of single lyophilized lots of standardized meals derived from the same specific formulation utilizing whole eggs and skim milk solids (5.7% by weight) averages approximately 107%. Hence, the $^{13}C$ signal and binding attributes of double lyophilization is consistent with single lyophilization. Therefore, Applicant has discovered that multiple lyophilization steps of the food component surprisingly does not hurt the binding and signaling capacity of $^{13}C$ and digestive characteristics of the meal.

As will be appreciated by those skilled in the art, the amount of algae or other source of $^{13}C$ to be added to the meal or component thereof will depend on a variety of factors including desired dosage, the amount of meal material, and the source of $^{13}C$. It is apparent that a plurality of meals can be produced simultaneously according to the freeze dry method. Once the marker is uniformly distributed in a meal or component thereof, individual servings can be produced by simply dividing the batch by weight, volume, or any other suitable technique, into individual servings.

There are several advantages to using the described processes to prepare standardized meals. Freeze-dried meals provide a vehicle of reliably and accurately incorporating a marker such as a stable isotope labeled material or drug into an edible food matrix. The marker or drug may be incorporated into the edible food during preparation or at the site where the meal will be re-constituted. Freeze-dried meals also assure standardization of tests across all medical users and sites of administration. Various biological markers or drugs, and combinations thereof, can be incorporated and evaluated from the same meal matrix. Refrigeration is not required for freeze-dried meals, which makes them easier to store and prevents spoilage.

It should be understood that the lyophilized delivery meal may be utilized to effectively and accurately incorporate and deliver any marker, isotope, or drug that is not susceptible to degradation during the lyophilization process so that the marker or drug maintains its functional activity once the delivery meal is reconstituted. Freeze-drying a standard meal wherein a marker or drug may be incorporated into one component of the meal may be used to deliver a marker or drug for use in any medical procedure where a physiological or diagnostic measurement is made following ingestion of a labeled edible food by the patient.

The standardized freeze dried meal may be used to assess gastric emptying in patients or test subjects. To utilize the meal, the clinical personnel simply reconstitute, generally with a specific amount of potable water, the pre-labeled meal prior to the test. In some cases, the meal may be heated or cooked following reconstitution. For example, a 27 g pouch of $^{13}C$-labeled lyophilized formulated whole egg meal may be re-hydrated with 4 ounces of water and cooked for 1.5 minutes in a microwave set at 1100 watts to form a uniformly labeled egg patty. The patient then ingests the meal, which includes the marker, for example, labeled algae. As the patient empties the meal to the small intestine, the $^{13}C$ label, and the accompanying food components, is absorbed and metabolized resulting in the production of labeled carbon dioxide, specifically $^{13}CO_2$. The $^{13}CO_2$ is excreted in the breath of the patient. Breath samples are collected by techniques known in the art, at periodic time intervals and the amount of $^{13}CO_2$ in the breath sample determined by techniques known in the art.

For accurate results of solid phase gastric emptying measurements, the marker must remain bound to the delivery vehicle, for example, an edible food component. If the marker becomes unbound it may move out in front of the solid phase emptying process into the liquid phase, passing through the pylorus and into the intestine faster than is representative of the actual solid phase gastric emptying process. Unbound marker may also pass through or be absorbed by the stomach wall and enter the circulation and metabolism process in a manner that gives rise to a $^{13}CO_2$ signal unrelated to the digestive process intended to be measured. Thus, it is important to ensure that the manufacturing process does not change the nature of raw materials to the extent that binding capacity is lost.

In diagnostic tests using $^{13}C$, the amount of $^{13}C$ administered must be precisely known. In a breath test, the results are based on the amount of $^{13}CO_2$ produced, which is directly related to the amount originally ingested. To determine the actual dosage of $^{13}C$, it is necessary to know the weight percentage of total carbon, as well as the percent of $^{13}C$ in the marker. This is shown in Table 1, which illustrates three different amounts of $^{13}C$ label target dosages when utilizing the $^{13}C$-labeled algae species *S. platensis*. The amount of $^{13}C$ labeled *S. platensis* that must be incorporated into a meal to achieve the target dose of $^{13}C$ is determined according to the following equation:

$$\text{Target dose mg }^{13}C/(^{13}C\text{-Atom \% X Total Carbon \%}) = \text{mg }[^{13}C]\text{-}S.\text{ platensis dispensed}$$

Table 1 provides several examples of how the equation is used. This calculation is applicable to $^{13}C$-labeled molecules or larger entities, such as a biomass.

TABLE 1

Example calculation of dispensing to achieve three target dose levels of $^{13}C$.

| Target Dose Mg $^{13}C$ | $[^{13}C]$-*S.p.* $^{13}C$-Atom % | $[^{13}C]$-*S.p.* % Carbon | $[^{13}C]$-*S.p.* mg | Tolerance ± mg |
|---|---|---|---|---|
| 80 | 0.95 | 0.42 | 200 | 20 |
| 40 | | | 100 | 10 |
| 20 | | | 50 | 5 |

For *S. platensis*, the carbon content will generally be about 42%, and the $^{13}C$ incorporation about 95%, as shown in the table above.

One may now perform a study with a sufficient number of patients to establish appropriate dosage to be added to a standardized meal. A specific example is to conduct a prospective cross-over study where a set of normal patients and a set equal in number of patients with known delayed gastric emptying are each administered the same meal 3 times on separate occasions with the meal remaining the same except for a different dosage of $^{13}C$ label as prescribed in the table above. The area under the $^{13}CO_2$ excretion curves from the normal and delayed emptying groups can be compared at the 3 different dose levels with appropriate statistical challenges to determine the lowest acceptable dose that provides sufficient signal to assess both normal and impaired (delayed) gastric emptying utilizing the intended meal. The meal can then be consistently formulated and produced containing the selected dosage.

Under circumstances where the marker or source of the marker and/or meal or component thereof is changed, it is desirable to validate the new (surrogate) marker or food. To fully validate the use of such a breath test among all pertinent patient populations, it is important to correlate the results obtained with the results that would be obtained using the gold standard scintigraphy test. Differences in the type of meal or marker used may give rise to different gastric emptying rates and different physiologic and metabolic footprints. While a mathematical relationship between the two meals may be established and the surrogate meal become a reliable predictor for $t_{1/2}$, the number of studies necessary to validate the relationship will be increased and it is possible that a consistent relationship will not occur between the predicate meal and the surrogate meal across all patient populations if the composition of each meal is significantly different. For example, in gastric emptying tests it is possible that two different meals or markers may have a consistent mathematical and physiological relationship in normal patients, but perhaps not in some affected patients. A high number of gastroparetics (patients who empty their stomach's slower than healthy individuals) are diabetic and diabetics may metabolize different meals in a manner that gives rise to some inconsistency in the predicted relationship between two different meals.

Simply matching the protein, carbohydrate and fat content of the surrogate meal to the predicate meal will not assure physiological consistency. The type of protein, carbohydrate and fat content may be different. For example, the protein in an egg meal may be primarily albumin, whereas a roll may contain primarily soy protein. Hence, the matrix binding the labels is different and subtle but important differences in trituration, absorption, and metabolism of the surrogate marker or drug may occur that will affect the proper classification of a patient.

To improve reliability in the validation process, the surrogate meal should match the predicate meal. In order for such a surrogate meal intended for widespread outpatient utilization to be highly reliable, safe and easily distributed it should be consistent in texture, composition and nutritional value to the predicate meal; have a consistent physiological and metabolic relationship to the predicate meal used to determine its efficacy; be safe from spoilage and decay; and have a commercially reasonable shelf life prior to utilization.

It is well known that there is significant, normal biologic variation in the rate of gastric emptying in humans. When utilizing gastric scintigraphy, repeated measurements of the gastric emptying rate using the same meal in the same subject show an ~12% coefficient of variation at critical measurement times during the emptying cycle. Hence, when one is preparing to validate a new marker against an established method, e.g., gastric scintigraphy, an important task is determining the degree of biologic variation observed with the new meal and new marker. This can be measured by conducting a clinical study in which subjects are given the same meal with the same marker in the same dosage on independent days. Upon completion, and for each subject, the individual variability is calculated by subtracting the rate of gastric emptying as measured on the first test administration from the rate of gastric emptying on the second test administration. One can then calculate the standard deviation (SD) and the % coefficient of variation (% CV) of the differences obtained from the study subjects. In a study of 73 subjects conducted by applicant for FDA approval of a lyophilized specifically formulated whole egg meal, the average SD of the differences in independent administrations of the test meal by $^{13}C$-labeled breath test across 5 critical time points in the gastric emptying cycle was 6. The % CV was 12%. When the same meal was utilized in an independent set of 28 patients assessed by gastric scintigraphy using the radionuclide label $^{99m}Tc$ at the same critical time points during the emptying cycle, the SD was 7 and the % CV was 11%. Hence, the meal is operating consistently across different populations and with different markers. This is an important method validation element. The table below shows the statistics at each time point and the average across all time points.

TABLE 2

Statistics at 5 Time Points (45 min, 90 min, 120 min, 150 min, and 180 min)

| Procedure | N | 45 Min | 90 Min | 120 Min | 150 Min | 180 Min | Avg |
|---|---|---|---|---|---|---|---|
| Sp. Breath Test SD | 73 | 4.0 | 6.8 | 6.8 | 5.9 | 5.1 | 5.7 |
| Sp. Breath Test % CV | 73 | 17.5 | 14.1 | 11.6 | 9.6 | 8.8 | 12.3 |

TABLE 2-continued

| | Statistics at 5 Time Points (45 min, 90 min, 120 min, 150 min, and 180 min) | | | | | | |
|---|---|---|---|---|---|---|---|
| Procedure | N | 45 Min | 90 Min | 120 Min | 150 Min | 180 Min | Avg |
| Scintigraphic SD | 28 | 7.2 | 8.0 | 7.1 | 6.3 | 4.9 | 6.7 |
| Scintigraphic % CV | 28 | 21.0 | 12.3 | 8.7 | 7.1 | 5.2 | 10.9 |

B.T. metric = kPCD
Scint metric = % emptied

The normal biologic variability associated with a specific meal is a critical characteristic of a standardized meal. If the degree of normal variability is not known, then the degree to which a therapeutic intervention can be deemed successful will be unknown or will be mistakenly understood. When a gastric emptying test is utilized for both diagnosis of gastroparesis (or other gastric emptying rate disorders) and subsequent monitoring of the patient's therapy, one must know the critical limit for detection of therapeutic effect to know if the therapy is working. Clinicians will rightfully ask: How much must the patient's gastric emptying rate increase in response to a therapeutic drug intended to speed up the stomach in order to know if the therapy is effective? In other words, how much must the rate of gastric emptying increase in order that the rate increase not to be due to simple normal, random biologic variation? The critical limit associated with a specifically formulated meal may be calculated using standard statistical equations, provided the degree of biologic variation is known.

It should be observed that the unique lyophilized approach to compounding and producing a standardized meal intended for measurements of gastric emptying is critical to the uniformity and consistency of the meal. Inconsistency may contribute to increased measurements of biologic variability and, hence, contribute to unnecessarily wide critical limits of therapeutic effect.

In an embodiment of the invention where a meal is used for assessing gastric emptying, both the predicate $^{99m}$Tc label or meal and the surrogate marker or meal may be incorporated into the same meal matrix. In this case the $^{99m}$Tc label must be added to the meal matrix at the site of administration due to its short radioactive-½ life-nature.

In one embodiment of the invention, the predicate meal is provided as the lyophilized standard pre-labeled meal described above. After the predicate meal is reconstituted, $^{99m}$Tc label is added so that the radiolabel and surrogate marker are bound in the same specifically formulated lyophilized food matrix. The patient or test subject then ingests the dual labeled meal and gastric emptying is measured simultaneously by the scintigraphy method previously described and the breath test. The two measurements thus obtained are compared against each other and mathematically correlated. Since both the radiolabel and surrogate marker are incorporated into the same matrix, this embodiment allows for the reliable validation of a predicate meal type or predicate marker. By doing so, both test are administered simultaneously eliminating the need to administer each test method independently on separate days. By putting both markers in the same specially formulated lyophilized meal and conducting each method concurrently, the effects of normal day to day biologic variation are eliminated, and, hence, correlation of the surrogate method to the predicate method is improved.

One advantage of establishing a lyophilized meal suitable for introduction of both a predicate and surrogate marker is that the meal may be used to test different dosages of labels to assure that there is sufficient label signal arising from the meal to make the appropriate physiologic or diagnostic conclusion. For example, prior to establishing a relationship between an established radioactive predicate label and a new non-radioactive $^{13}$C surrogate label, the appropriate dose of $^{13}$C to be incorporated in the meal to provide a reliable $^{13}$CO$_2$ excretion rate in the patient must be determined. The signal must be readily measurable providing reliable data from which to establish the mathematical relationship between the predicate and surrogate marker.

According to another embodiment, both a surrogate meal and predicate meal are prepared according to the lyophilization process described above to prepare a surrogate meal matching a like-prepared predicate meal. In this embodiment, meals having identical edible food components (that is, the same edible food in the same amounts in each meal, prior to the incorporation of any label into the meal) containing no marker is reconstituted and the predicate label and surrogate marker are each added at the time of reconstitution. Both the predicate meal and the surrogate meal intended to be tested in clinical studies will be prepared with the same pre-label contents and in the same manner. Alternatively, if the surrogate label is stable, that is, capable of maintaining its functional activity post lyophilization, it may be added to a meal prior to lyophilization.

The development of a surrogate meal that can be used to reliably validate the use of a surrogate marker or drug that is similar in texture, composition and nutritional value to a predicate meal and that may be readily incorporated into a commercially available meal/delivery system will allow for the substitution of stable non-radioactive labels for radioactive labels in test meals. Thus, in assessing physiological conditions such as gastric motility in women of childbearing age and in children where radiation exposure is undesirable, stable, non-radioactive markers may be used.

A multitude of assessments may be done using the gastric emptying markers described herein such as predicate and surrogate marker comparisons, measurement of intra-patient gastric motility variation, inter-patient comparisons, establishment of normal ranges for gastric emptying in healthy individuals, establishment of cutoff points for differentiating normal from impaired subjects, establishment of critical limits of therapeutic efficacy, and the like.

Once validated against a well-characterized predicate method, e.g., gastric scintigraphy, a surrogate, non-radioactive labeled lyophilized meal as described herein is well suited for diagnostic testing in the clinical setting. However, of particular importance is its use in heretofore difficult to perform large-scale epidemiological studies. Gastric scintigraphy is expensive, radioactive and requires specialized facilities and equipment. Aside from excessive cost, it cannot be used in epidemiological studies in children and women of childbearing age. Meals produced by the methods described herein are ideally suited to studies in which large populations may be simply, conveniently and safely tested to determine the prevalence of various gastric motility impairments. For example, the prevalence of gastroparesis as described in the medical literature varies highly because only a very limited number of small studies have been performed due to the limitations of gastric scintigraphy. Utilization of a $^{13}$C-labeled standardized meal produced and validated in the way described herein may be conveniently and safely given to various populations suspected of gastroparesis in numbers sufficient to statistically validate the true prevalence of gastroparesis. Because the test is standardized, it may be given in a wide array of populations and locations. For example, it is thought that gastroparesis occurs primarily in diabetics, non-ulcer functional dyspepsia patients and in subsets of GERD (gastroesophageal reflux disease) patients. These populations may now be safely and conveniently tested in an outpatient epidemiological setting.

Ideally, the edible foods of the surrogate, predicate, or meals used in the clinical setting of the invention are prepared in a controlled food and/or pharmaceutical manufacturing environment meeting appropriate regulatory standards and have long term packaging stability with easy and reliable re-constitution techniques. In order to be used commercially for the diagnosis and monitoring of gastric emptying, absorption or metabolic disorders in humans, the gastric emptying meals with related markers are required by law to be produced in compliance with current good manufacturing practices applicable to pharmaceutical products since the product "will be used in the diagnosis or mitigation of disease." Production methods must comply with the FDA's Quality System and Drug Manufacturing Regulations. These meals must meet specific safety, uniformity, controlled manufacturing, stability, labeling and packaging requirements to be legally distributed and considered non-adulterated product. Most importantly, the diagnostic consistency and reliability of the product is assured. An important regulatory parameter is the uniformity of the dosage intended to be delivered to the patient. Appropriate sampling of the final dosage form of the meal must meet a label uniformity standard of <6.0% relative standard deviation (% RSD).

Lyophilization techniques facilitate this process. The preparation of these lyophilized meals in a manufacturing environment of this type ensures that the raw materials of the meals will not be randomly prepared at the site of test administration, which may lead to inaccuracies. For example, inconsistencies may arise from site to site due to differences in grocery type supplies, differences in cooking methods and times, and test administration techniques. Further, the use of a manufacturing process to prepare the edible food is beneficial because it allows not only for the production of a more "standardized" meal, but for wide scale commercial use of the edible foods with an appropriate biological marker or drug consistent with regulatory requirements. For those meals that must be cooked at the testing site, it is best that the same method of cooking be applied to the predicate meal and the surrogate meal to minimize uncertainty. A freeze-dried standardized meal of the invention can serve as a standardized delivery mode for therapeutic drugs. Similarly an array of freeze-dried standardized meals of the invention can be used to study the absorption of various diagnostic and/or therapeutic drugs with varying meal compositions. Further, a freeze-dried standardized meal incorporating markers and/or therapeutic and diagnostic drugs can be used for animal studies in which food components, dosage of label or drug and amount of food by weight must be delivered with reliable control. In an embodiment of the invention, once a surrogate meal with its surrogate marker or drug has been established as useful by comparison to a predicate meal with the predicate marker or drug, freeze drying the edible food components of the meal ensures not only the stability of the meal but the reproducibility of the test results obtained with such standardized meals.

While several embodiments described herein show the use of a freeze-drying method of preparing the edible foods of the meals, it would be apparent to one skilled in the art that any method guaranteeing that the surrogate meal is identical in composition to the predicate meal can be used. For example, the edible food components may be prepared by baking of the edible components into a roll or biscuit in accordance with a standardized process and the predicate marker or drug and the surrogate marker or drug may be incorporated into the meal during a controlled manufacturing process or at the site of the test.

The invention will be further described with reference to the following non-limiting Examples. It will be apparent to those skilled in the art that many changes can be made in the embodiments described in the Examples without departing from the scope of the present invention. Thus, the scope of the present invention should not be limited to embodiments described in this application, but only by the embodiments described by the language of the claims and the equivalents of those embodiments.

EXAMPLE 1

Preparation of $^{13}$C Pre-labeled Standardized Egg Meals 207.41 kg (amount required to prepare 2,000 meals) of pasteurized, de-sugared whole egg liquid formula containing whole eggs, water, nonfat dry milk, salt, and smoke flavoring was thoroughly mixed with 200 g of $^{13}$C-labeled *S. platensis* containing 95% atom % $^{13}$C and 42% total carbon. The amount of liquid egg formulation required to produce a specific number of meals of 28 g was calculated from the following equation:

(Amount of units)×(28 g/0.27)=grams of liquid egg formulation.

The necessary amount of labeled algae depends on the percentage of $^{13}$C present in the algal cells and was calculated from the following equation:

$^{13}$C/($^{13}$C-atom %×Carbon %)=mg [$^{13}$C]-*S. platensis*

The total amount of labeled algae required was calculated by the following equation:

Number of doses×mg [$^{13}$C]-*S. platensis*/dose

The liquid egg formulation containing the appropriate amount of thoroughly mixed label was pumped onto pre-chilled anodized aluminum lyophilization trays and lyophilized for 24 hours with a initial temperature of −20° C. and a final temperature of 48° C. under <200 microns of pressure, to meet a loss on drying (LOD) specification of <3.0% moisture content. The resulting freeze-dried labeled mixture was divided to produce 2,000 units of meals of uniform weight and label distribution.

EXAMPLE 2

Confirmation of Uniform Distribution of Marker

Ten samples were randomly pulled from approximately the beginning, middle, and end points in the milling process from a manufacturing run that was prepared to produce units each containing 6 mg $^{13}$C derived from [$^{13}$C]-*S. platensis*. An aliquot of each sample was analyzed in a combustion chamber attached to an isotope ratio mass spectrophotometer and compared to a known $^{13}$C standard.

The samples had a mean recovery of 6.01 mg per sample, a standard deviation of 0.072, and a % relative standard deviation of 1.19%. These results demonstrate that the $^{13}$C label was uniformly distributed in the meal matrix.

EXAMPLE 3

Confirmation of Uniform Distribution of Marker in Meals Prepared On-site

In some instances it may be desirable to provide the freeze dried meal and label separately so that the label may be mixed with the meal just prior to use. However, uniform distribution of the label remains of significant importance.

To determine whether manual, on-site mixing yields acceptable uniform distribution of the marker a quantity of [$^{13}$C]-S. platensis and liquid egg formulation were freeze-dried separately as described above. A 50 mg aliquot of dried [$^{13}$C]-S. platensis was rehydrated in 5 g of water in a 20 mL glass vial with a Teflon lined screw cap, shaken vigorously for 1 minute and added to a 28 g of egg powder. 88 g of water was used to rinse the content of the [$^{13}$C]-S. platensis rehydration vial and added to the egg mix. The rehydrated egg mix was then stirred vigorously for 1 minute and cooked in a microwave for 1.5 minutes. The cooked egg meal was then allowed to cool, and separated into 6 samples. The above meal preparation was done in triplicate.

Each of the 6 slices of each the 3 meals were dried and ground into uniform samples via mortar and pestle. An aliquot was removed from each sample and combusted and assayed by gas isotope ratio mass spectrometry and the amount of $^{13}$C determined by comparison to a known standard.

The % relative standard deviation across the 6 samples from each of the 3 meals was 5.2%, 3.4%, and 3.3% respectively. These results demonstrate that on-site mixing produced meals with uniformly distributed marker.

EXAMPLE 4

Evaluation of Binding Capacity 28 g of lyophilized egg powder containing a known quantity of $^{13}$C-marker was reconstituted with 93 g of water, mixed, and cooked. The cooked meal was cooled, weighed and pressed through a 4 mm screen into a collection pan. Ten gram samples were collected, dried overnight at 105° C., and ground by mortar and pestle into a fine powder. Duplicate aliquots of the dried sample were combusted and assayed by gas isotope ratio mass spectrometry.

Eighty percent of the portion of egg meal that remained in the pan after the screening procedure was divided into 2 equal amounts and subjected to in vitro digestion. U.S.P. gastric fluid was prepared by dissolving 2.0 g of NaCl$_2$ and 3.2 g of purified pepsin derived from porcine stomach mucosa with an activity of 800-2500 units/mg protein in 7.0 mL of hydrochloric acid. The volume was brought to 1 L with water and the pH brought to approximately 1.2.

The egg meal portions were incubated in 100 mL of the prepared gastric solution at 37° C. for 30 minutes with constant stirring at a fixed rate of 200±20 rpm using a stainless steel paddle apparatus located approximately 0.25 in from the bottom of the flask. After digestion, the contents of each flask were poured over a stacked set of 4 mm, 2 mm, and 1 mm screens and rinsed with cool tap water for 1 minute at a rate of approximately 4 L/min and the screening stack allowed to drain for 5 minutes.

The weight of digested meal remaining on each screen was recorded and isolated in tared aluminum sample pans. The samples were dried over night at 105° C. to remove excess water.

An aliquot of the 1 mm sample (representative of the smallest size a food particle reaches after the full trituration process) was analyzed for $^{13}$C by combustion and ratio mass spectrometry. The $^{13}$C content of these samples was compared to the $^{13}$C content of the pre (non) digested samples. The percent binding was calculated according to the following equation:

$$(^{13}\text{C content per gram of Carbon post-digested meal})/(^{13}\text{C content per gram of Carbon pre-digested meal}) \times 100$$

Percent binding was 100% in the 1 mm digested samples compared to the pre-digested samples with 51% of the overall egg mass lost during in vitro digestion.

While preferred embodiments of the present invention have been described, it should be understood that various changes, adaptations and modifications may be made therein without departing from the spirit of the invention and the scope of the appended claims.

What is claimed is:

1. A method of producing a lyopohilized product labeled with a marker comprising the sequential steps of:
   providing a marker;
   uniformly distributing a known amount of said marker throughout an edible food component, the edible food component comprising egg white and egg yolk; and
   lyophilizing the marker and the edible food component,
   wherein the marker is a $^{13}$C marker derived from a biomass, and wherein the marker binds to both the egg white and the egg yolk.

2. The method of claim 1, wherein the biomass is *Spirulina platensis*.

3. The method of claim 2, wherein the *Spirulina platensis* is grown in a $^{13}$C-enriched environment.

4. The method of claim 1, wherein the whole eggs are part of a liquid egg formulation.

5. The method of claim 1, further comprising reconstituting the marker and edible food component and adding a radioactive isotope.

6. The method of claim 5, wherein the radioactive isotope is $^{99m}$Tc sulphur colloid.

7. The method of claim 1, wherein the edible food component is lyophilized and reconstituted prior to uniformly distributing a known am out of the marker throughout the edible food component.

8. The method of claim 7, wherein the edible food component comprises whole eggs, and the whole eggs are lyophilized into an egg powder, and then rehydrated into liquid eggs.

9. A method of producing a lyophilized product labeled with markers comprising the sequential steps of:
   providing a first marker and a second marker, the first marker comprising a $^{13}$C marker derived from a biomass and the second marker comprising a radioactive isotope;
   uniformly distributing a known amount of the first marker throughout an edible food component, the edible food component comprising egg white and egg yolk;
   lyophilizing the first marker and the edible food component;

reconstituting the first marker and the edible food component;

adding the second marker to the first marker and the edible food component, wherein the first marker binds to both the egg white and the egg yolk.

10. The method of claim 9, wherein the biomass is *Spirulina platensis*.

11. The method of claim 10, wherein the *Spirulina platensis* is grown in a $^{13}$C-enriched environment.

12. The method of claim 9, wherein the second marker is $^{99m}$Tc sulphur colloid.

13. The method of claim 9, wherein the whole eggs are part of a liquid egg formulation.

14. The method of claim 9, wherein the edible food component is lyophilized and reconstituted prior to uniformly distributing a known am out of the marker throughout the edible food component.

15. The method of claim 14, wherein the edible food component is lyophilized into an egg powder, and then rehydrated into liquid eggs.

16. A method of producing a lyophilized product labeled with a marker comprising the sequential steps of:
providing egg white and egg yolk;
lyophilizing the egg white and egg yolk;
reconstituting the egg white and egg yolk;
adding a marker to the reconstituted egg white and egg yolk; and
lyophilizing the marker and the reconstituted egg white and egg yolk, wherein the marker is a $^{13}$C marker derived from a biomass, and wherein the marker binds to both the egg white and the egg yolk.

17. The method of claim 16 wherein the lyophilized product has a % binding recovery that is substantially equal to a % binding recovery of a control meal, wherein the control meal comprises a lyophilized edible food component that has been lyophilized only once.

18. The method of claim 17 wherein the % binding recovery is at least 100%.

19. The method of claim 16 further comprising dividing the lyophilized product into sub-batches after lyophilizing the edible food component, and wherein the reconstituting the edible food component comprises reconstituting one or more sub-batches.

20. The method of claim 16, wherein the biomass is *Spirulina platensis*.

21. The method of claim 16, wherein the edible food component comprises whole eggs.

22. A meal comprising:
an edible food component;
a known amount of a marker uniformly distributed throughout the edible food component, said marker being a $^{13}$C marker derived from a biomass and chosen so that when ingested by a mammal with the meal either the absorption or metabolism of the marker may be monitored and correlated to a physiological function of the mammal or a therapeutically effective amount of the marker delivered to the mammal;
wherein the edible food component has been lyophilized and reconstituted before said known amount of marker is uniformly distributed throughout the edible food component, and wherein the edible food component and the marker have been lyophilized together after said known amount of marker is distributed throughout the edible food component, so that the edible food component has been lyophilized at least twice, wherein the edible food component comprises egg white and egg yolk, and wherein the marker is bound to both the egg white and egg yolk.

23. The meal of claim 22, wherein the meal has a % binding recovery that is substantially equal to the % binding recovery of a control meal, wherein the control meal comprises an edible food component that has been lyophilized only once.

24. The meal of claim 22, wherein the meal has a % binding recovery that is at least 100%.

25. The meal of claim 22, wherein the whole eggs are part of a liquid egg formulation.

26. The meal of claim 22, wherein the biomass is $^{13}$C-enriched *Spirulina platensis*.

27. The meal of claim 22 packaged into a unit dose form.

28. The meal of claim 22, wherein the physiological function is function selected from the group consisting of a metabolic function and a digestive function.

29. The meal of claim 28, wherein the physiological function is the rate of gastric emptying.

30. The meal of claim 22, further comprising a known amount of a radioactive isotope chosen so that when ingested by a mammal with the meal either the absorption or metabolism of the radioactive isotope may be monitored and correlated to a physiological function of the mammal, wherein the radioactive isotope has been added to the meal after the edible food component and the marker have been reconstituted.

31. The meal of claim 30, wherein the radioactive isotope is $^{99m}$Tc sulphur colloid.

32. A meal comprising egg white and egg yolk, wherein the egg white and egg yolk are bound to a known amount of a $^{13}$C marker derived from a biomass, said $^{13}$C marker chosen so that when ingested by a mammal with the meal either the absorption or metabolism of the marker may be monitored and correlated to a physiological function of the mammal or a therapeutically effective amount of the marker delivered to the mammal, wherein the egg white and egg yolk have been lyophilized and reconstituted before the $^{13}$C marker is added to the egg white and egg yolk, and wherein the egg white and egg yolk and $^{13}$C marker have been lyophilized together after the marker is added to the egg white and egg yolk, so that the egg white and egg yolk have been lyophilized at least twice.

33. The meal of claim 32, wherein the meal has a % binding recovery that is substantially equal to the % binding recovery of a control meal, wherein the control meal comprises whole eggs that have been lyophilized only once.

34. The meal of claim 33, wherein the meal has a % binding recovery that is at least 100%.

35. The meal of claim 32, wherein during trituration in a mammal's stomach substantially all of the $^{13}$C marker remains bound to the egg white and egg yolk.

36. The meal of claim 32, wherein the egg white and egg yolk are part of a liquid egg formulation.

37. The meal of claim 32, wherein the $^{13}$C marker is uniformly distributed throughout the egg white and egg yolk.

38. The meal of claim 32, wherein the biomass is $^{13}$C-enriched *Spirulina platensis*.

39. The meal of claim 33 packaged into a unit dose form.

40. The meal of claim 32, wherein the physiological function is selected from the group consisting of a metabolic function and a digestive function.

41. The meal of claim 40, wherein the physiological function is the rate of gastric emptying.

42. The meal of claim 32, further comprising a known amount of a radioactive isotope chosen so that when ingested by a mammal with the meal either the absorption or metabolism of the radioactive isotope may be monitored and correlated to a physiological function of the mammal, wherein the radioactive isotope has been added to the meal after the egg white and egg yolk and the $^{13}C$ marker have been reconstituted.

43. The meal of claim 42, wherein the radioactive isotope is $^{99m}Tc$ sulphur colloid.

* * * * *